United States Patent
Kuriyama et al.

(10) Patent No.: US 7,394,084 B2
(45) Date of Patent: Jul. 1, 2008

(54) METHOD OF GENERATING IMAGE AND ILLUMINATION DEVICE FOR INSPECTING SUBSTRATE

(75) Inventors: Jun Kuriyama, Fukuchiyama (JP); Masato Ishiba, Kyoto (JP); Kiyoshi Murakami, Kyoto (JP); Teruhisa Yotsuya, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 11/157,749

(22) Filed: Jun. 20, 2005

(65) Prior Publication Data
US 2006/0000989 A1    Jan. 5, 2006

(30) Foreign Application Priority Data
Jun. 30, 2004    (JP) ............................. 2004-192855

(51) Int. Cl.
G01B 11/24    (2006.01)
(52) U.S. Cl. ............................. 250/559.34; 250/559.46; 356/394
(58) Field of Classification Search ............ 250/559.34, 250/559.08, 559.2; 362/249; 356/237.4, 356/237.1
See application file for complete search history.

(56) References Cited

U.S. PATENT DOCUMENTS

| | | | | |
|---|---|---|---|---|
| 6,273,338 B1 * | 8/2001 | White | ................ | 235/462.42 |
| 6,542,236 B1 * | 4/2003 | Kim | ...................... | 356/394 |
| 6,598,994 B1 | 7/2003 | Tait et al. | | |
| 7,019,826 B2 * | 3/2006 | Vook | ................. | 356/237.1 |
| 2002/0114505 A1 | 8/2002 | Mahon et al. | | |

FOREIGN PATENT DOCUMENTS

| | | |
|---|---|---|
| EP | 1363153 A1 | 11/2003 |
| JP | 62-127617 | 6/1987 |
| JP | 64-066546 | 3/1989 |
| JP | 01-282410 | 11/1989 |
| JP | 02-076080 | 3/1990 |
| JP | 04-166710 | 6/1992 |
| JP | 04-166711 | 6/1992 |
| JP | 05-248820 | 9/1993 |
| JP | 2005-184246 | 8/1994 |
| JP | 06-300702 | 10/1994 |
| JP | 09-201044 | 8/1996 |
| JP | 10-318730 | 12/1998 |
| JP | 11-249020 | 9/1999 |
| JP | 2000-121563 | 4/2000 |
| JP | 2001-068900 | 3/2001 |
| JP | 2001-153808 | 6/2001 |
| JP | 2003-139712 | 5/2003 |

OTHER PUBLICATIONS

Japanese Utility Model No. 59-85905, *Pattern Recognition Device*, filed Nov. 6, 1984.

* cited by examiner

*Primary Examiner*—Georgia Y. Epps
*Assistant Examiner*—Tony Ko
(74) *Attorney, Agent, or Firm*—Weaver Austin Villeneuve & Sampson LLP (57) ABSTRACT

For generating an image for inspection of a substrate, a camera is provided above this substrate with an optical axis orienting downward and a plurality of multi-colored light emitting members are set around the optical axis of the camera so as to be within a specified angular range with respect to a target area on the substrate. The camera is operated to generate an image of the target area for inspection while switched-on conditions of these light emitting members are being controlled such that the colors and angles of light illuminating this target area are varied according to a specified kind of the purpose of this inspection.

12 Claims, 7 Drawing Sheets

| SECTION | NORMAL SOLDER INSPECTION | PRECISION SOLDER INSPECTION | CHARACTER INSPECTION | PRE-MOUNTING INSPECTION |
|---|---|---|---|---|
| A | RED | RED | (OFF) | ORANGE |
| B | GREEN | YELLOW | | |
| C | | GREEN | WHITE | (OFF) |
| D | BLUE | CYAN | (OFF) | BLUE |
| E | | BLUE | | |

METHOD OF GENERATING IMAGE AND ILLUMINATION DEVICE FOR INSPECTING SUBSTRATE

Priority is claimed on Japanese Patent Application 2004-192855 filed Jun. 30, 2004.

BACKGROUND OF THE INVENTION

This invention relates to the production of a substrate having components mounted thereto and more particularly to the technology of carrying out an inspection by image processing, either during or after a production process therefor, of the lands, the soldered parts and the mounted components on the substrate that is being produced or has been produced.

The present inventors have previously developed an apparatus for automatically inspecting soldered portions on a substrate by the image processing technology making use of the mirror reflection property of such soldered portions, as described in Japanese Patent Publication Tokko 6-1173. The optical system of this previously developed inspection apparatus comprises three circular ring-shaped light sources having different diameters and a two-dimensional color camera (hereinafter simply referred to as a camera). These three light sources are respectively adapted to emit a beam of red, green and blue light, and the camera is disposed at a position corresponding to the center of these light sources with its optical axis vertically oriented. With an inspection apparatus thus structured, each of the light sources is positioned so as to have a different angle of elevation from the position of a solder portion to be inspected. Each beam of light projected onto the surface of the solder portion undergoes a mirror reflection but the kind of mirror-reflected light received by the camera changes according to the sloping angle of the light-reflecting surface of the solder. Thus, the three colors of the light sources become distributed on the solder portion of the obtained image along the direction in which this sloping angle changes. Thus, if the pattern of each color that would appear on the image of a well-shaped solder surface is preliminarily registered and compared with color patterns that are actually obtained from a target surface, it is possible to judge the quality of the target surface for inspection.

With an illumination device of the type described above and adapted to project light beams of three primary colors, however, the range of angle in which the light beam of each color is projected is fixed and hence the corresponding relationship between each color and the angle of slope also becomes fixed. As a result, if the slope of a solder fillet becomes very steep, it becomes difficult to display the color distribution reflecting the change in this slope. Accordingly, a color change may not be obtained from the image corresponding to a fillet and it becomes difficult to detect its slope.

SUMMARY OF THE INVENTION

It is therefore an object of this invention in view of the above to improve the accuracy of inspection on soldered portions of a substrate by using an improved illumination device having an illuminating system of the same structure although the portion of the object to be inspected and/or the purpose of inspection may change.

It is another object of this invention to improve the resolution related to the extraction of sloping angles for inspecting a solder surface condition based on its mirror-reflection characteristic.

According to a method of this invention for generating an image for inspection of a substrate, an image-taking means is provided above this substrate with an optical axis orienting downward and a plurality of multi-colored light emitting members are set around the optical axis of this image-taking means so as to be within a specified angular range with respect to a target area on the substrate. The image-taking means is operated to generate an image of the target area for inspection while switched-on conditions of these light emitting members are being controlled such that the colors and angles of light illuminating this target area are varied according to a specified purpose of this inspection.

In the above, the angle with respect to the target area of inspection may be taken as the angle between the line connecting the center of the target area of inspection with the light-emitting member and the substrate surface (or the angle of elevation), or the angle between the optical axis of the image-taking means and the light-emitting member. This is also the same regarding the angle of illumination.

The image-taking means is preferably a two-dimensional color camera. The multi-colored light emitting means are preferably each a light emitting diode (also referred to as light emitting device) comprising red, green and blue light emitting elements (monochromatic LEDs) but may be light emitting means of other kinds such as electroluminescence elements.

For an inspection of the kind making use of mirror-reflected light, such as the so-called solder inspection, it is preferable to set the plurality of light emitting members such that they do not interfere with the extraction of sloping angles. For example, if the range of angles can be estimated for the slope on the solder surface, a range may be determined for the direction in which light should be emitted such that mirror-reflected light from slopes within this estimated range can be dependably received by the image-taking means and the light emitting members are arranged within the range thus determined.

By this method, an image for inspection can be generated by adjusting the positions of the image-taking means and the group of light emitting members such that the portion of the substrate to be inspected will be included in the area of which an image will be taken. According to this invention, the color of light for illuminating this inspection area and the angle of illumination can be adjusted according to the kind and the purpose of the inspection by properly selecting the light emitting members to be switched on and the color of light to be emitted by them.

When the so-called solder inspection is to be carried out after the soldering process has been completed on the substrate to be inspected, the switched-on conditions of the light emitting members are controlled such that light of different color will be switched on in each of the plurality of sections corresponding to different angular ranges with respect to the target area. By such a control, a plurality of beams of light with different colors can be emitted from different directions so as to obtain an image with a color distribution indicative of the sloping condition of the solder. In the above, the target area may be considered to be surrounding the optical axis of the image-taking means according to the distribution of the light emitting members.

In such a solder inspection process, the number of sections and the angular range of the target area may be varied and the combination of colors of light to be switched on can be adjusted according to the purpose of the inspection to be carried out. If the required level of resolution is not very different from the situation of aforementioned Japanese Patent Publication Tokko 6-1173, for example, it is sufficient to set three sections for light of red, green and blue to be switched on. If the sloping condition of the target solder surface is desired to be inspected more in detail, the number of sections may be increased to four or more such that light with as many different colors can be switched on. When a solder surface with steeper slopes is inspected, a plurality of sections may be set in the angular range closer to the substrate surface than to the image-taking means.

Light of any color may be associated with each section but it is preferable to make adjustments such that colors change according to the so-called "hue circle" along the direction in which the angle with respect to the substrate surface changes. If there are five sections, for example, the colors of light for the sections may be set such that the color will change from red to yellow to green to cyan to blue in this order along the direction in which angles change. If the colors are so chosen, the image data obtained by the image-taking means can be converted to color phase (hue) data, and the sloping condition of the substrate surface can be easily grasped from the direction in which the color phase data increase or decrease, as well as from the magnitude of their change.

When characters printed on a component (or its package) on a substrate are inspected, the switched-on conditions of the light emitting members may be controlled such that the target area of inspection is illuminated diagonally thereby from above with white light. If characters are printed in white on a black package, only diffused light from the characters printed in white is led to the image-taking means and reflected light from the black package surface which is nearly in the mirror-surface condition is not received by the image-taking means. As a result, an image with a strong contrast between white and black can be generated.

When lands and cream solder on a substrate are inspected before components are mounted thereto, accuracy of image processing for extracting an inspection area can be improved by projecting light of a color close to that of the target area from a direction suitable for its observation.

An inspection apparatus for a substrate according to this invention may be characterized as comprising an image-taking means above the substrate to be inspected with an optical axis orienting downward, an illuminating means having a plurality of multi-colored light emitting members disposed around the optical axis of the image-taking means so as to be within a specified angular range with respect to a target area on the substrate, an inspecting means for inputting an image obtained by the image-taking means while the target area is illuminated by the illuminating means and carrying out an inspection by image processing on a specified portion of the obtained image, and an illumination control means for controlling switched-on conditions of the light emitting members so as to vary the colors and angles of light illuminating the target area according to the purpose of the inspection carried out by the inspecting means.

In the above, the image-taking means and the light emitting members are as described above. The illuminating means may further include a box structure for covering these light emitting members as well as circuits for controlling them. The inspecting means and the illumination control means may each be a computer, storing a program for executing own processes. The inspecting means may further include an external memory for storing programs for the inspection, set data and standard images of target areas. The illumination control means may further include a driver circuit for directly controlling the switching operations of the light emitting members based on commands from its computer. The inspecting means and the illumination control means may be realized either by a single computer or by separate computers.

With an inspection apparatus of this invention thus formed, the manner of control over each light emitting member of the illuminating means can be switched automatically or by a manual setting according to an input of data indicative of the details of the inspection.

According to a preferred embodiment of the invention, the illuminating means includes a circuit for controlling the light emitting members by dividing them into a plurality of sections having different angular ranges with respect to the target area, and the illumination control means is adapted to control their switched-on conditions in units of these sections. With an inspection apparatus thus structured, it is possible to change the switched-on conditions and to assign colors in units of these sections having different angular ranges with respect to the target area. Thus, sections to be switched on may be selected according to the kind of inspection to be carried out and to illuminate each section by light of a different color. It now goes without saying that it is also possible to illuminate a plurality of mutually adjacent sections in the same color.

According to a further preferable embodiment of the invention, the illuminating means includes light emitting diodes containing red, green and blue light emitting elements serving as the light emitting members and also a matrix circuit connecting these light emitting elements in a matrix formation. The illumination control means is further adapted to switch on these light emitting diodes in units of the sections by time-sharing within an exposure period of the image-taking means. In the above, the light emitting diodes may be of any type such as the chip type or the lamp type.

These embodiments are based on the characteristics of light emitting diodes that it is possible to quickly switch them on and off. For example, the control circuit may be formed by connecting together the anodes of the light emitting elements emitting the same color and the cathodes in units of the sections. If it is desired to illuminate a specified section in a specified color, for example, the cathodes of the light emitting elements in that section are connected to 0V and the anodes of those light emitting elements corresponding to that color to a specified voltage. Regarding the above, it goes without saying that the connecting relationships of the cathodes and anodes may be interchanged. The individual light emitting elements may be connected either on their cathode or anode side by dividing them into a plurality of groups.

If three of these sections (say, A, B and C) are selected and three specified colors (say, red, green and blue) are respectively assigned to them, the light emitting elements may be so controlled that sections A, B and C will be switched on sequentially within the period of a single exposure of the image-taking means such that an image showing a color distribution according to the sloping condition on the target area can be obtained.

When such an apparatus is used to inspect a substrate after it has been soldered, two or more of these sections may be used and the light emitting elements may be controlled such that the inspection area is illuminated with light with a plurality of colors in directions with different angular ranges. In this case, each of the selected sections may be illuminated in different colors or a plurality of mutually adjacent sections may be illuminated in the same color.

When characters printed on a component mounted to the substrate (or on its package), the inspection apparatus may be controlled so as to use at least one of these sections such that the inspection area is illuminated diagonally from above with white light. This may be done by selecting just one section or a plurality of mutually adjacent sections and causing white light to illuminate the selected section or sections.

An illumination device embodying this invention for inspecting a substrate may be characterized as comprising a plurality of multi-colored light emitting members disposed with elevation angles from below within a range greater than a specified value around a space of a specified size and a control circuit for controlling these light emitting members in units of sections having different ranges of elevation angles. Such an device may be placed above the target substrate to be inspected and may have an image-taking means disposed so as to have its optical axis passing through the center of the space surrounded by the light emitting members with the image taking surface facing downward. Such an illumination device may also be connected to a computer for controlling its switching on and off.

With an illumination device thus characterized, a suitable illumination condition can be set according to the type of inspection to be carried out because such a computer can select the switched-on condition of each section and adjust the color of light assigned to each of the sections to be switched on. It also goes without saying that an illumination device embodying this invention can be used not only with an inspection apparatus of an automatic type described above but also with an apparatus for visual inspection.

According to this invention, a suitable illumination condition can be established according to the type of inspection to be conducted and hence various kinds of inspection can be carried out with a high level of precision. It also makes it possible to use a single inspection apparatus for carrying out inspections of different types.

In the case of inspection of a soldered portion, in particular, the present invention is convenient because the resolution for extraction of sloped surface can be varied easily and hence both simple and detailed inspections can be carried out according to the purpose of inspection.

DETAILED DESCRIPTION OF THE INVENTION

Figure 1:
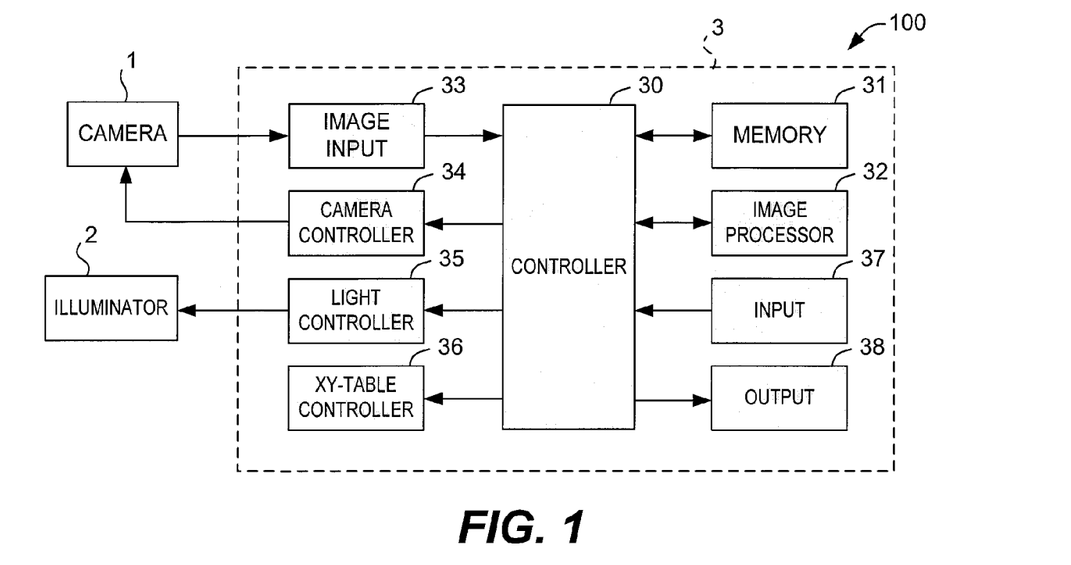
FIG. 1 is a block diagram of an inspection apparatus embodying this invention for a substrate.

FIG. 1 is a block diagram of an inspection apparatus 100 embodying this invention for the inspection of a substrate having components mounted thereto during and after its production process, adapted to carry out inspections of different kinds such as the so-called "pre-mounting inspection" for inspecting the conditions of lands and cream solder before components are mounted to the substrate, the so-called "character inspection" for judging, after components have been mounted, whether the mounting of the components has bee done correctly by checking the printed characters on them or on their packages, and the so-called "solder inspection" carried out on a substrate after soldering has been completed for determining whether the sloping condition of solder fillets is good or not.

The inspection apparatus 100 has a camera 1, an illuminator 2 and a control unit 3 as its main components and may additionally include a substrate stage (not shown) for supporting a substrate to be inspected.

In the above, what was simply referred to as the camera 1 is a CCD camera for generating two-dimensional stationary color images. The illuminator 2 is an illumination device having a plurality of full-color LED lamps as will be described more in detail below, adapted to project light of different colors selectively.

The control unit 3 comprises a controller 30 which is a computer having a CPU, a ROM and a RAM as its main constituents and to which are connected a memory 31, an image processor 32, an image input device 33, a camera controller 34, a light (illumination) controller 35, an XY-table controller 36, an input device 37 and an output device 38.

In the above, the memory 31 is a non-volatile memory device such as a hard disk, storing programs that are necessary for the inspection, set data regarding the inspection area and standard images inside the inspection area. The memory 31 may be used also for the purpose of saving image data used for the inspection and results of the inspection.

The image processor 32 is an LSI that incorporates circuits such as a binarization circuit and a differentiation circuit used for image processing and is adapted to carry out a specified processing by receiving image data from the controller 30 and to output the results of the processing back to the controller 30.

The image input device 33 includes an interface circuit corresponding to the camera 1 and an A/D converter circuit. The camera controller 34 includes a circuit that generates driver signals to the camera 1. The light controller 35 includes a driver circuit for carrying out a voltage control such that the illuminator 2 will light up according to a specified illumination pattern. The XY-table controller 36 is for the purpose of moving an XY-table (not shown) that is set upon the aforementioned substrate stage.

The input device 37 may comprise a keyboard and a mouse and is used for the purpose of selecting the kind of inspection to be carried out by this inspection apparatus 100 and inputting various data that are necessary for the inspection. The output device 38 is for outputting the results of the inspection and may comprise a printer or an interface circuit to an external apparatus.

When a selection is inputted through the input device 37 as explained above, the controller 30 thereby acknowledges the kind of inspection to be done and makes use of the light controller 35 to carry out illumination according to a specified pattern. As a target substrate to be inspected is brought onto the substrate stage, the XY-table controller 36 is used to adjust the positional relationship of the substrate with respect to the camera 1 and the illuminator 2, and the camera 1 is operated while the illuminator 2 illuminates the substrate. The image obtained by the camera 1 is subjected to a digital conversion by means of the image input device 33 and stored on the RAM within the controller 30. The controller 30 sets an inspection area at a target inspection position based on the image data and while the image within this area is processed by the image processor 32, a judgment process is carried out relative to the selected kind of inspection.

Figure 2:
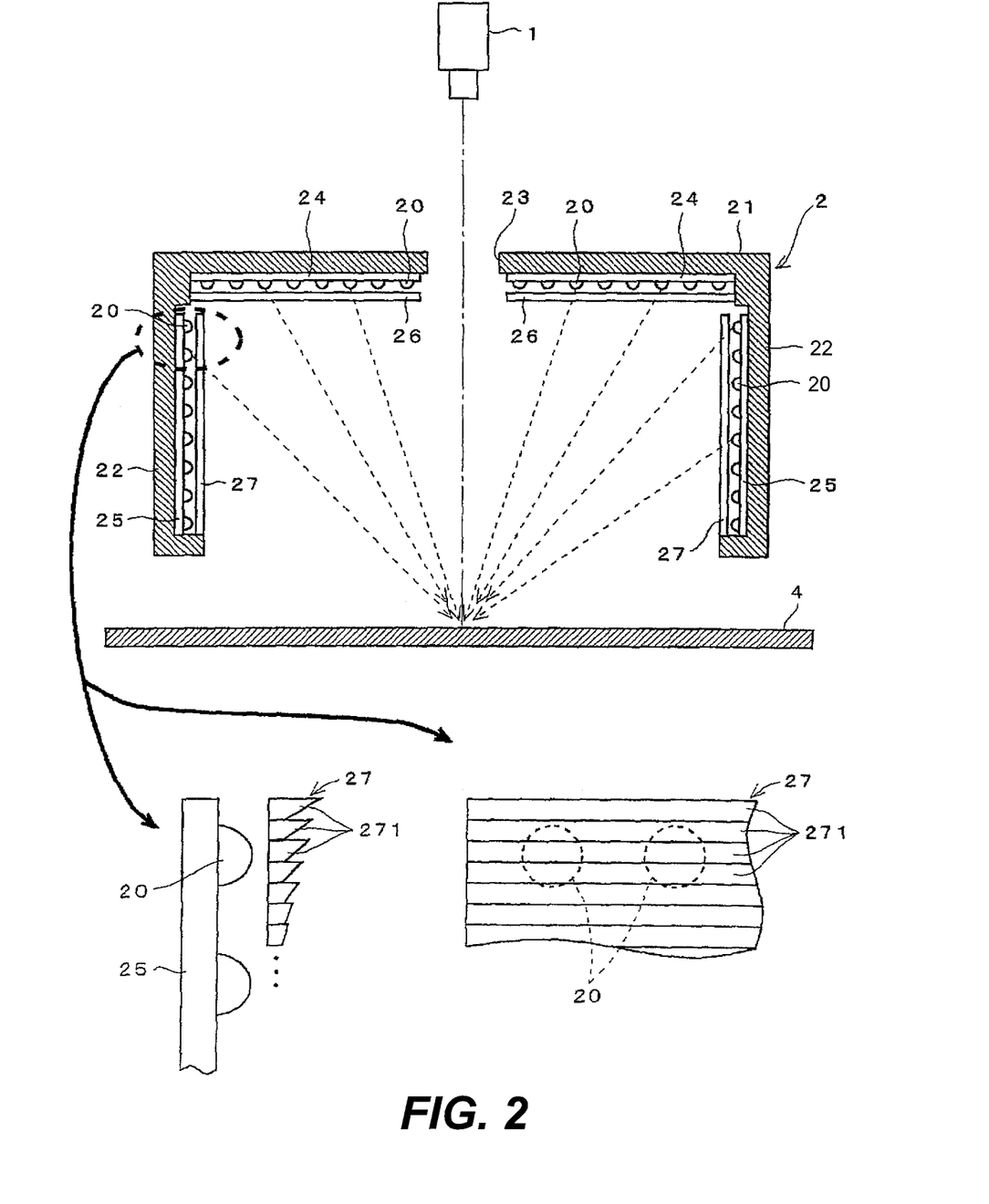
FIG. 2 is a sectional view of an illumination device embodying this invention, inclusive of a side view and a front view of a light-collecting plate.
Figure 3:
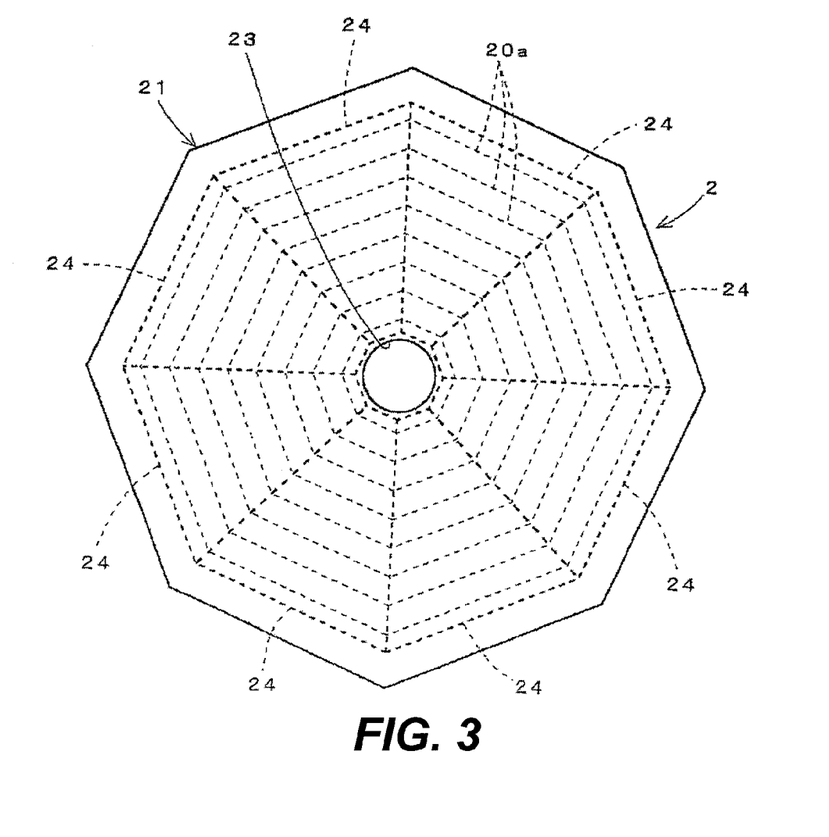
FIG. 3 is an external view of the illumination device taken from above.

FIG. 2 shows the internal structure of the illuminator 2 together with its positional relationship with a substrate 4 and the camera 1. FIG. 3 is an external view of the illuminator 2 as seen from above. As shown, the illuminator 2 has a box structure comprised of an octagonal upper plate 21 and side walls 22 each integrally formed with a corresponding one of the edges of the upper plate 21. This box structure is open on the bottom side. A circular peephole 23 is formed at the center of the upper plate 21. The camera 1 is disposed exactly above this peephole 23 with its optical axis oriented vertically downward.

Eight trapezoidal substrates 24 are attached to the inner surface of the upper plate 21 corresponding individually to its eight sides, each substrate 24 carrying thereon a plurality of full-color LED lamps (hereinafter simply referred to as LED lamps) 20 together with their wirings. Since the LED lamps 20 each comprise red (R), green (G) and blue (B) light emitting elements, a full-color beam of light can basically be emitted from each of these LED lamps 20 by controlling the lighting of each light emitting element.

On each of the trapezoidal substrates 24, a plurality of mutually parallel lines 20a are defined as shown in FIG. 3 in the direction of the width, and specified number of these lamps 20 are arranged on these lines 20a. A vertical substrate 25 with a plurality of such LED lamps 20 arranged thereon in a matrix form is attached to the inner surface of each of the side walls 22.

Light-collecting (condenser) plates 26 and 27 made of an acrylic resin material are disposed in front of the trapezoidal and vertical substrates 24 and 25. These light-collecting plates 26 and 27 are each made as a Fresnel lens and approximately in the same shape and size of the substrate 24 or 25 behind.

FIG. 2 includes a side view and a front view of one of these light-collecting plates 27. As can be seen, the light-collecting plate 27 according to the illustrated embodiment is formed with a plurality of narrow and elongated transparent pieces 271 each having a sloped surface on the front side, arranged along the longitudinal direction and mutually attached together. The sloped surfaces on the front side are such that they recede backward on the downward side. The angles of the sloped surfaces are adjusted to vary gradually from the top to the bottom. Although not separately illustrated, the light-collecting plates 26 on the trapezoidal substrates 24 are also structured similarly, each comprising a plurality of narrow and elongated pieces having a sloped surface on one side with the angles of their sloped surfaces varying gradually.

With the light-collecting plates 26 and 27 thus structured and thus positioned, the light beams emitted from the LED lamps 20 are collected at a target area immediately below the peephole 23. Each of these light-collecting plates 26 and 27 is secured to the inner surface of a corresponding one of the side walls 22 by means of a fastening means (not shown).

Figure 4:
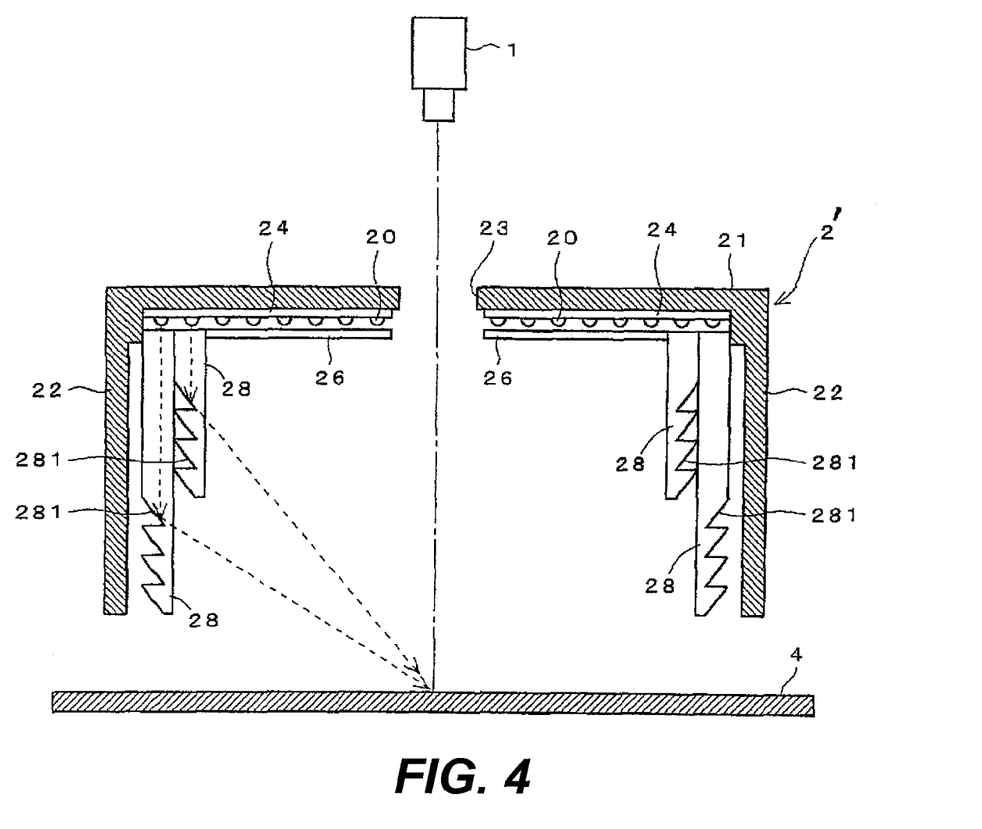
FIG. 4 is a sectional view of another illumination device embodying this invention.

FIG. 4 shows another illuminator 2' according to another embodiment of the invention, like components being indicated by the same numerals as in FIG. 2 for convenience and repetitious explanations being omitted for simplicity of description. This illuminator 2' shown in FIG. 4 is different from the illuminator 2 described above with reference to FIG. 2 in that the LED lamps 20 are only on the substrates 24 on the inner surface of the upper plate 21 and that a specified number (two according to the example in FIG. 4) of light-conducting members 28 connected to the light-collecting plate 26 are disposed in front of each substrate 24.

These light-conducting members 28 are planar members made of an acryl resin material, disposed perpendicularly to the surface of the upper plate 21 at positions of the outer edges of the substrates 24. Their lengths are such that the outer members are longer (extending further downward) than the inner members. A plurality of forwardly sloping steps 281 are formed on the lower part of the outer surface of each light-conducting member 28. Light from the LED lamps 20 travels downward inside the light-conducting member 28 but is reflected on the inner surfaces of these steps 281 and is led towards the inspection area. Thus, light reaches the inspection area also from sideways although the LED lamps 20 are not provided on the side walls 22 according to this embodiment. Moreover, since light can be sent sideways at a lower position from the light-conducting members 28 closer to the side walls 22, the paths of light reaching the inspection area become approximately the same as by the illuminator 2 shown in FIG. 2.

Figure 5:
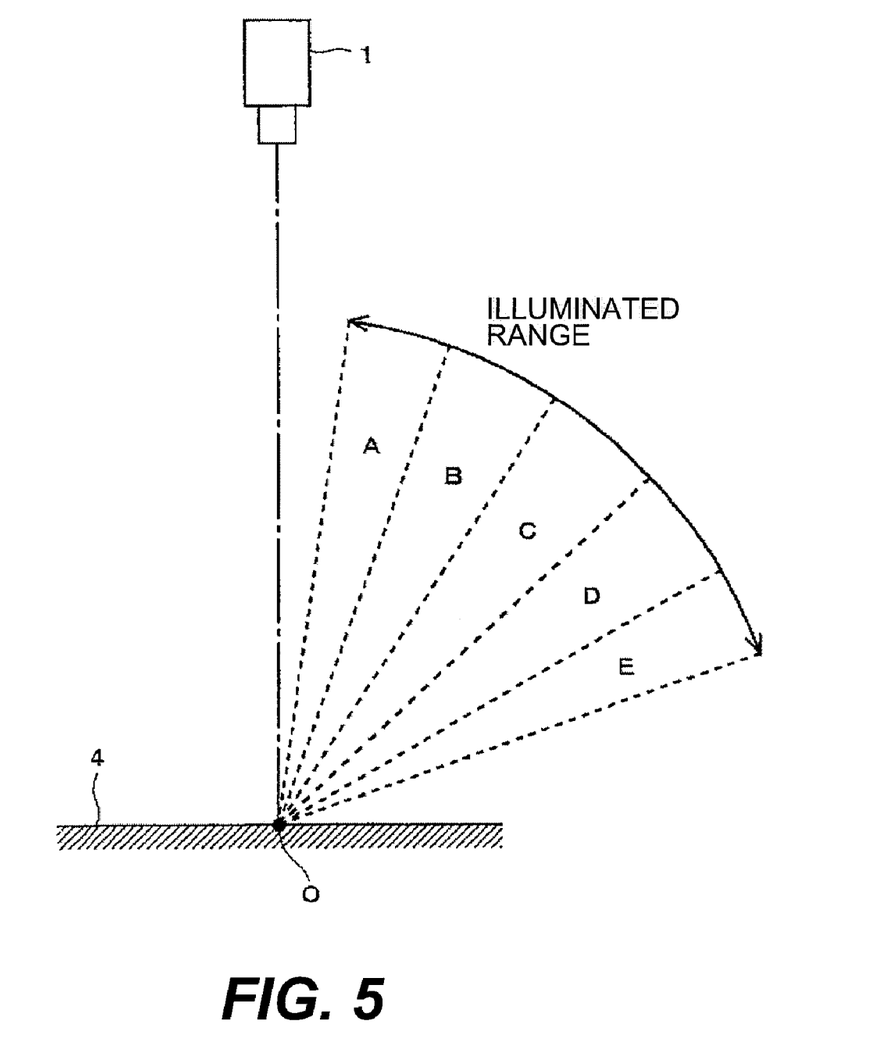
FIG. 5 is a drawing for showing the range of angles in which light can be projected onto the inspection area.

FIG. 5 shows the range of angles in which light can be projected onto the center point O of the inspection area when the illuminator 2 or 2' described above is used. In the case of a solder inspection according to the illustrated example of the invention, an angular range within which light that is mirror-reflected from the sloped surface of a solder portion can be received by the camera 1 is preliminarily determined and the LED lamps 20 are set within this range of angles.

According to the example shown in FIG. 5, the angular range within which light can be illuminated is divided into five sections A, B, C, D and E in the increasing order of the angle of elevation as seen from the center position O of the inspection area. The control of switching on and off the LED lamps 20 is effected in units of these sections.

Figure 6:
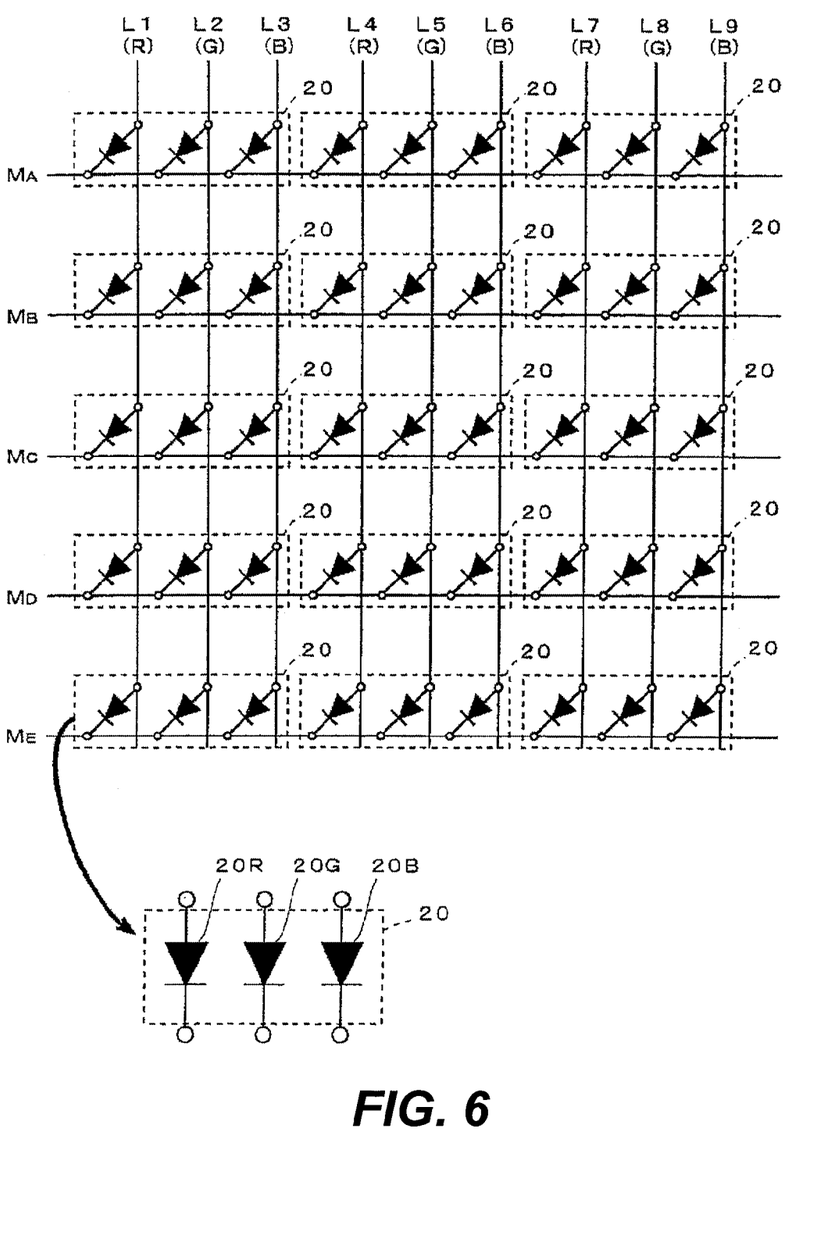
FIG. 6 is a circuit diagram of a circuit for the LED lamps.

FIG. 6 shows an example of circuit structure that may be used for this control. According to this example, each of the LED lamps 20 has a red (R) light emitting element 20R, a green (G) light emitting diode 20G and a blue (B) light emitting diode 20B and each of these diodes 20R, 20G and 20B has two terminals. The control circuit is formed by connecting the anodes of the individual light emitting elements 20R, 20G and 20B together for each color and their cathodes are connected together for each of the sections A, B, C, D and E such that a matrix formation is formed.

Although FIG. 6 shows a structure wherein three LED lamps 20 are included in each of the sections A, B, C, D and E, an actual circuit may be formed by providing an independent circuit for each substrate. The number of connecting lines within each circuit may be adjusted according to the number of sections corresponding to the substrate or the number of LED lamps 20.

Of the lines connected to anodes in the circuit shown in FIG. 6, lines L1, L4 and L7 are connected to the red light emitting elements 20R, lines L2, L5 and L8 are connected to the green light emitting elements 20G and lines L3, L6 and L9 are connected to the blue light emitting elements 20B. Lines $M_A$, $M_B$, $M_C$, $M_D$ and $M_E$ that are connected to the cathodes respectively correspond to the sections A, B, C, D and E.

The light controller 35 carries out the illumination control in units of sections by switching the voltage or impedance of each line. Explained more in detail, those of the lines $M_A$, $M_B$, $M_C$, $M_D$ and $M_E$ that correspond to sections to be switched on are connected to a voltage line at 0V while those of the lines L1-L9 corresponding to the desired color are connected to the line at the power source voltage. If "red" is assigned to Section A, for example, line $M_A$ is connected to 0V and lines L1, L4 and L7 are connected to the source voltage. Those lines not corresponding to any of the sections to be switched on (lit) or to any of the colors assigned to a section to be switched on are set at a condition of high impedance.

When the same color is assigned to two or more sections, those of lines $M_A$, $M_B$, $M_C$, $M_D$ and $M_E$ corresponding to sections to be switched on are connected to 0V and those of lines L1-L9 corresponding to the selected color are connected to the source voltage.

When different colors are to be assigned to each of two or more sections, these sections must be switched on sequentially. In this case, it is necessary to partition one single exposure period of the camera 1 into a plurality of switched-on periods for the different sections to be lit such that light of each of the different colors must be reflected onto a single sheet of obtained image.

Figure 7:
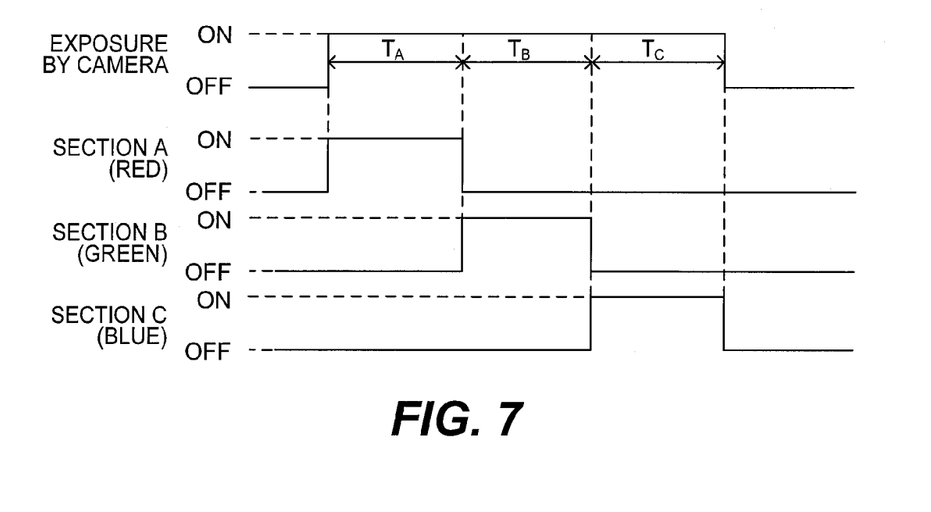
FIG. 7 is a time chart for showing an example of control for switching on light of different colors.

FIG. 7 shows an example of such partition of exposure time of the camera 1 for switching on light of different colors. In this example, colors of red, green and blue are respectively assigned to sections A, B and C. A single exposure period of the camera 1 is therefore divided into three time segments $T_A$, $T_B$ and $T_C$ corresponding respectively to the three colors of red, green and blue. Light emitting element R in section A is switched on during time segment $T_A$, light emitting element G in section B is switched on during time segment $T_B$ and light emitting element B in section C is switched on during time segment $T_C$. In this case, too, if the same color is assigned to a plurality of sections, light of the same color can be switched on in the plurality of sections as explained above.

These LED lamps 20 as described above can be used to cause white light to be emitted by switching on all of the light emitting elements 20R, 20G and 20B. It is also possible to cause not only white light but also light of colors other than the three primary colors to be emitted by sequentially switching on a plurality of kinds of light emitting elements within a switched-on period. The color of emitted light can be varied by adjusting the combination of the light emitting elements to be switched on and the ratio of the lengths of the switched-on periods. Thus, if white or a color other than the three primary colors is assigned to a specified section, the light controller 35 will sequentially switch on two or more light emitting elements selected corresponding to the assigned color within the switched-on period.

In summary, the on/off condition and the color of each LED lamp 20 are controlled in units of sections according to this embodiment of the invention, and the controller 30 of the control unit 3 controls the switching of each section such that an optimum condition of illumination can be established according to the kind of inspection to be carried out.

Figure 8:
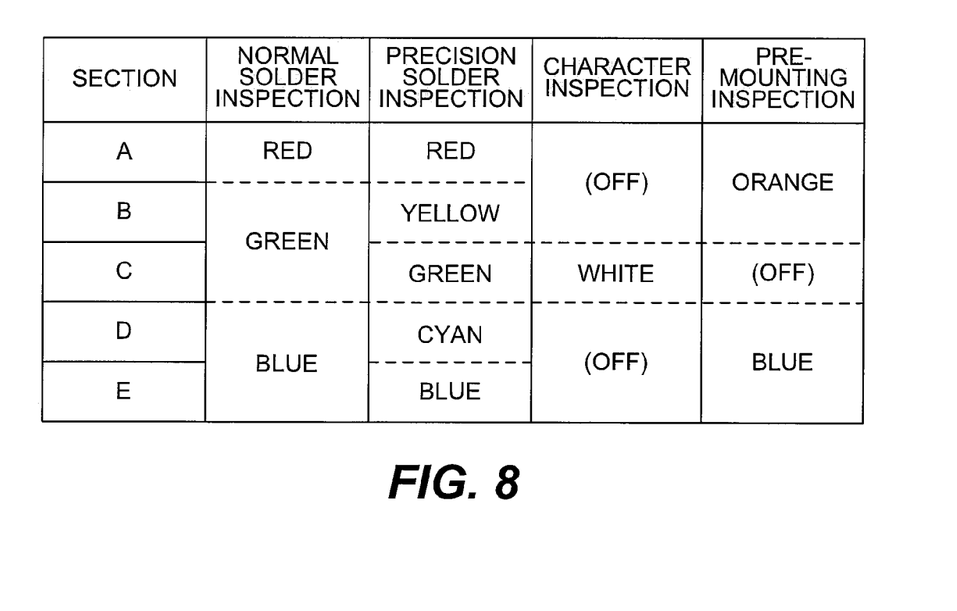
FIG. 8 is a table of illumination patterns for different kinds of inspection.

FIG. 8 shows an example of illumination patterns that may be set for each kind of inspection to be carried out. Such a table may be electronically stored, say, in the memory 31.

In the table, "Normal Solder Inspection" means the conventional inspection by using the distribution of the three primary colors. In the illustrated example, red light is used for section A, green light is used for sections B and C, and blue light is used for sections D and E. By this kind of inspection, a sloped solder surface can be inspected with the same level of accuracy as by the method described in aforementioned Japanese Patent Publication Tokko 6-1173.

By the so-called "Precision Solder Inspection", by contrast, different colors of light are used for sections A-E such that variations in the sloping angle of the solder in an image can be analyzed more precisely in detail. According to the illustrated example, red, yellow, green, cyan and blue are respectively assigned to sections A-E.

Figure 9A:
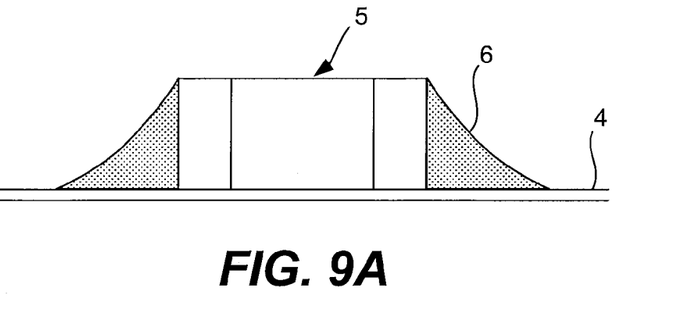
FIG. 9A is a side view of a chip component soldered to a substrate.
Figure 9B:
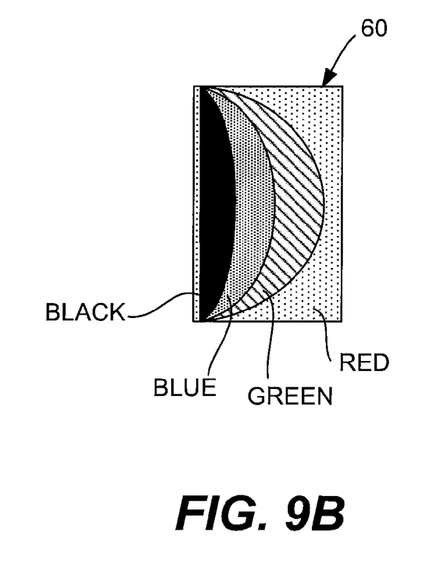
FIGS. 9B and 9C are images obtained for the inspection of this chip component.
Figure 9C:
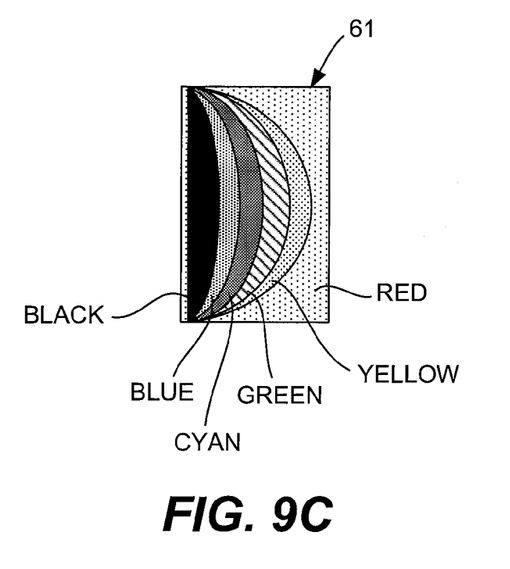

FIG. 9A shows a chip component 5 soldered to the substrate 4, numeral 6 indicating a fillet. FIG. 9B shows an image 60 of the fillet 6 on one side of the chip component 5 obtained by the aforementioned normal solder inspection. FIG. 9C shows another image 61 of the same fillet 6 obtained by the aforementioned precision solder inspection. On these two images 60 and 61, the positions and sizes of the red portions and the black portions that result because light does not reach are the same but the portions between the red and block portions are quite different. On the image 60 by the normal solder inspection, there are only two color portions with blue and green between the red and black portions. On the image 61 by the precision solder inspection, by contrast, there are four different colors (blue, cyan, green and yellow) appearing between the red and black portions. This means that the sloped condition of the fillet 6 can be more accurately distinguished.

The precision solder inspection may be carried out by dividing the target inspection area (or the image 61 of FIG. 9C) and setting for each pixel allowable ranges of the quantity of received for red, green and blue light at the time of a teaching process. The quantity of received red, green and blue light by each pixel is detected and it can be thereby determined whether the fillet is of an allowable shape or not by checking whether received light of each color is within the allowable range or not.

In the case of a fillet having a very steep slope, only blue reflected light may be obtained by the normal solder inspection but cyan reflected light may be additionally obtained by the precision solder inspection such that it can be determined more reliably whether the fillet has a correct shape or not.

By the "Character Inspection", with reference again to FIG. 8, only section C is illuminated with white light, the other sections being not illuminated. In other words, printed characters can be illuminated diagonally from above with white light. By a conventional method of illumination, it was difficult to read printed characters because the printed surface is nearly in the condition of a mirror surface and regularly reflected light from such a surface is received by the camera. If white light is made incident only from section C, as shown in FIG. 8, regularly reflected light from the package surface is not received by the camera. Since only the white light that is reflected from the printed characters and is highly diffusive is received by the camera, a highly contrasting image of printed characters can be obtained.

By the "Pre-mounting Inspection", sections A and B are illuminated with orange light and sections D and E are illuminated with blue light, while section C is not illuminated. Before components are mounted, reflected light is obtained from the areas printed with cream solder. As for the areas not printed with cream solder, reflected light is obtained from lands having a color of copper. According to this example, lands having a color of copper is illuminated with orange light which is similar to the lands in color and the bluish cream solder is illuminated with blue light. Moreover, the relatively reflective lands are illuminated with orange light from above while the cream solder which tends to reflect light diffusively is illuminated with blue light from a sideward direction. With the illumination thus effected, areas with cream solder and areas with lands can be clearly distinguished such that any incompletely printed solder positions can be accurately detected.

With an inspection apparatus according to this invention, as explained above, a suitable illumination condition can be set according to the purpose (type) of inspection to be carried out because the pattern of illumination can be varied freely and a highly precise inspection can be effected. In the case of inspecting solder conditions, in particular, the slopes of fillets can be accurately analyzed and much more precise inspection can be effected than was possible by the prior art technology.

It goes without saying that a normal solder inspection and a precise solder inspection can both be carried out on a single substrate, depending on the kinds of components mounted thereto. FIG. 8 is not intended to limit the manner in which the control should be effected. Many variations are possible according to the object of inspection. When a fillet with steep slopes is inspected, for example, red, green and blue may be assigned respectively to sections C, D and E such that the angular changes of the fillet can be easily extracted.

What is claimed is:

1. A method of generating an image for inspection of a substrate, said method comprising the steps of:

providing an image-taking means above said substrate in an inspection process selected from the group consisting of inspection of land and cream on said substrate before components are mounted thereonto, inspection of characters printed on a component mounted onto said substrate and inspection of solder on said substrate after a soldering process, with an optical axis orienting downward;

providing a plurality of multi-colored light emitting devices each having a plurality of red, green and blue light-emitting elements around said optical axis of said image-taking means such that the illumination angle between the optical axis of said image-taking means and said light emitting device is within a specified angular range with respect to a target area on said substrate;

providing a control circuit for illuminating a specified target area with light of a specified color by switching on said device according to the kind of said inspection process so that the colors and angles of light illuminating said target area vary depending on specified types of inspection; and generating an image that is suitable for the type of said inspection being carried out on said substrate by projecting light of said specified color to said target area from specified ones of said light-emitting elements at projection angles within a specified one of a plurality of ranges by applying a specified voltage to anodes of said specified light-emitting elements within said specified range.

2. The method of claim 1 wherein said inspection is for the inspection of said solder on said substrate after said soldering process; and wherein light with different colors are projected on said solder from different ones of said light-emitting elements at different ones of said plurality of ranges by applying specified voltages to corresponding ones of said anodes.

3. The method of claim 1 wherein said inspection is for inspecting characters printed on said component mounted onto said substrate; and wherein white light is projected diagonally from upward directions on said characters by switching on selected ones of said light-emitting elements corresponding to said upward directions by applying specified voltages to anodes of said selected light-emitting elements, and switching off selected ones of said light-emitting elements not corresponding to said upward directions by applying specified voltages to anodes of said selected light-emitting elements.

4. The method of claim 1 wherein said inspection is for inspecting land and cream on said substrate; and wherein orange light is projected from above and blue light is projected horizontally on said substrate by applying a specified voltage to anodes of those of selected groups of light-element elements projecting light from above and horizontally onto said substrate.

5. An apparatus for inspection of a substrate, said apparatus comprising:

an image-taking means above said substrate with an optical axis orienting downward;

a plurality of multi-colored light emitting devices each having a plurality of red, green and blue light-emitting elements around said optical axis of said image-taking means such that the illumination angle between the optical axis of said image-taking means and said light emitting device is within a specified angular range with respect to a target area on said substrate;

a control circuit for illuminating a specified target area with light of a specified color by switching on said device according to the kind of said inspection so that the colors and angles of light illuminating said target area vary depending on specified types of inspection; anodes of said light-emitting elements being connected together for each color; cathodes of said light-emitting elements being connected together for each of a plurality of angular ranges; and an inspecting means for inputting an image that is suitable for the type of said inspection being carried out on said substrate and is obtained by said image-taking means while said target area is illuminated by said device and carrying out said inspection by image processing on a specified portion of said obtained image.

6. The apparatus of claim 5 wherein said light-emitting elements are disposed with elevation angles from below within a range greater than a specified value around a space of a specified size; and said control circuit controls said light-emitting elements in units of sections having different ranges of elevation angles.

7. A method of generating an image for inspection of a substrate, said method comprising the steps of:

providing an image-taking means above said substrate in an inspection process selected from the group consisting of inspection of land and cream on said substrate before components are mounted thereonto, inspection of characters printed on a component mounted onto said substrate and inspection of solder on said substrate after a soldering process, with an optical axis orienting downward;

providing a plurality of multi-colored light emitting devices each having a plurality of red, green and blue light-emitting elements around said optical axis of said image-taking means such that the illumination angle between the optical axis of said image-taking means and said light emitting device is within a specified angular range with respect to a target area on said substrate;

providing a control circuit for illuminating a specified target area with light of a specified color by switching on said device according to the kind of said inspection process; and generating an image that is suitable for the type of said inspection being carried out on said substrate by projecting light of said specified color to said target area from specified ones of said light-emitting elements at projection angles within a specified one of a plurality of ranges by applying a specified voltage to cathodes of said specified light-emitting elements within said specified range.

8. The method of claim 7 wherein said inspection is for the inspection of said solder on said substrate after said soldering process; and wherein light with different colors are projected on said solder from different ones of said light-emitting elements at different ones of said plurality of ranges by applying specified voltages to corresponding ones of said cathodes.

9. The method of claim 7 wherein said inspection is for inspecting characters printed on said component mounted onto said substrate; and wherein white light is projected diagonally from upward directions on said characters by switching on selected ones of said light-emitting elements corresponding to said upward directions by applying specified voltages to cathodes of said selected light-emitting elements and switching off selected ones of said light-emitting elements not corresponding to said upward directions by applying specified voltages to cathodes of said selected light-emitting elements.

10. The method of claim 7 wherein said inspection is for inspecting land and cream on said substrate; and wherein orange light is projected from above and blue light is projected horizontally on said substrate by applying a specified voltage to cathodes of those of selected groups of light-element elements projecting light from above and horizontally onto said substrate.

11. An apparatus for inspection of a substrate, said apparatus comprising:

an image-taking means above said substrate with an optical axis orienting downward;

a plurality of multi-colored light emitting devices each having a plurality of red, green and blue light-emitting elements around said optical axis of said image-taking means such that the illumination angle between the optical axis of said image-taking means and said light emitting device is within a specified angular range with respect to a target area on said substrate;

a control circuit for illuminating a specified target area with light of a specified color by switching on said device according to the kind of said inspection; cathodes of said light-emitting elements being connected together for each color; anodes of said light-emitting elements being connected together for each of a plurality of angular ranges; and an inspecting means for inputting an image that is suitable for the type of said inspection being carried out on said substrate and is obtained by said image-taking means while said target area is illuminated by said device and carrying out said inspection by image processing on a specified portion of said obtained image.

12. The apparatus of claim 11 wherein said light-emitting elements are disposed with elevation angles from below within a range greater than a specified value around a space of a specified size; and said control circuit controls said light-emitting elements in units of sections having different ranges of elevation angles.

* * * * *